us007663745B2

(12) United States Patent
Zaman et al.

(10) Patent No.: US 7,663,745 B2
(45) Date of Patent: Feb. 16, 2010

(54) PLURAL LIGHT SOURCE AND CAMERA TO DETECT SURFACE FLAWS

(75) Inventors: Kamran Uz Zaman, Pittsford, NY (US); Stanley Pietrzykowski, Brighton, NY (US); Dante Pietrantoni, Rochester, NY (US); Kenneth Gottschalk, West Henrietta, NY (US); Richard Schichler, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 586 days.

(21) Appl. No.: 11/673,054

(22) Filed: Feb. 9, 2007

(65) Prior Publication Data

US 2008/0192243 A1     Aug. 14, 2008

(51) Int. Cl.
*G01N 21/00* (2006.01)
(52) U.S. Cl. ............... 356/237.2; 356/600; 356/612
(58) Field of Classification Search .......... None
See application file for complete search history.

(56) References Cited

U.S. PATENT DOCUMENTS

| 4,794,264 | A | 12/1988 | Quackenbos et al. |
| 4,794,265 | A | 12/1988 | Quackenbos et al. |
| 5,225,890 | A * | 7/1993 | Lee et al. .............. 356/237.2 |
| 6,100,990 | A * | 8/2000 | Ladewski ............... 356/445 |
| 6,157,450 | A | 12/2000 | Marchese-Ragona et al. |
| 7,099,002 | B2 | 8/2006 | Ishiura et al. |

* cited by examiner

*Primary Examiner*—Gregory J Toatley, Jr.
*Assistant Examiner*—Juan D Valentin
(74) *Attorney, Agent, or Firm*—Pepper Hamilton LLP (57) ABSTRACT

A method for detecting specular surface flaws on a coated substrate includes impinging visible non-integrated electromagnetic radiation from a first source onto the coated substrate, reflecting the visible non-integrated electromagnetic radiation off the coated substrate into a first photosensitive device, forming a recorded high frequency surface flaw image, and impinging visible coherent electromagnetic radiation from a second source onto a coated substrate at an oblique angle. The visible non-integrated electromagnetic radiation and the visible coherent electromagnetic radiation on the coated substrate are collocated but not combined on the substrate. The visible coherent electromagnetic radiation is reflected off the coated substrate onto a screen material to form a low frequency surface flaw image. The low frequency surface flaw image is recorded to form a recorded low frequency surface flaw image.

20 Claims, 8 Drawing Sheets

PLURAL LIGHT SOURCE AND CAMERA TO DETECT SURFACE FLAWS

CROSS-REFERENCE TO RELATED APPLICATIONS

Not applicable.

STATEMENT REGARDING FEDERALLY SPONSORED RESEARCH

Not applicable.

NAMES OF PARTIES TO A JOINT RESEARCH AGREEMENT

Not applicable.

SEQUENCE LISTING

Not applicable.

BACKGROUND

1. Technical Field

The disclosed embodiments generally relate to systems and methods for detecting flaws in coated articles.

2. Description of the Related Art

In the process of electrophotographic imaging, a photoconductive member is electrically charged to a uniform potential. The charged member is exposed to a light image of the original document. The light selectively discharges areas on the surface, while leaving other areas uncharged, thus producing an electrostatic latent image. A developer material, typically containing charged toner particles with opposite polarity as that of the photoconductive member, is brought into contact with the exposed photoconductive member. The charged toner particles are transferred to oppositely charged areas on the photoconductive member's surface to form a visible image. An electrostatically charged substrate, such as a blank copy sheet, is brought into contact with the photoconductive member containing the toner particles, and the toner particles are transferred to the copy sheet. The toner particle image on the blank copy sheet is then heated to permanently affix the toner particles to the sheet to form a "hard copy" image.

Electrophotographic imaging members are well known in the art. An electrophotographic drum is typically used in copiers and printers, and it includes an electrically conductive hollow cylindrical metal substrate in the form of a tube. Typically, the tubes are made from aluminum or other reflective material. To achieve the desired dimensional properties required for these devices, the aluminum tubes are often machined on a lathe and left with a specular or mirror surface, which produces congruent reflection upon exposure to radiation.

The electrophotographic drums of this nature are coated, typically with several layers of coating material, with at least one of the coating layers including an organic photoconductive ("OPC") coating. These "layered photoreceptors" have at least a partially transparent photosensitive or photoconductive layer overlying a conductive ground plane, which typically may be the machined mirrored aluminum tube itself. The layers may be single-layered or multi-layered, such as members having an inner layer of undercoat material and outer layer of change transport material. The tube may be rough or honed, and it may be made of other materials, such as other metals or conductive polymers.

Uniformity of the substrate surface and the coated substrate surface is critical for producing clear images in the electrophotographic process. Uniformity of the outermost transparent or at least partially transparent coating (collectively referred to herein as "transparent coating") is particularly critical for color electrophotographic imaging. Typically, the transparent coating mean thickness may be about 20 µm to about 30 µm. The transparent coating can have coating thickness defects ranging from about 1 µm to about 30 µm. Submicron-sized defects are also possible, while larger defects are possible with thicker coatings.

Coating thickness defects can be in the form of "dimples" which have a coating thickness lower than the mean coating thickness, or "bumps" which have a thickness greater than the mean coating thickness. The coating defects may appear as circumferential banding. When visible electromagnetic radiation, or light, is impinged upon these coating defects at an oblique angle, there is little or no light scattering; the reflection from these coating defects is primarily specular, that is there is a mirror angle reflection. These coating defects in general are referred to as low frequency specular surface flaws due to the subtle nature of the change in coating thickness that accompanies these defects and to the mirror angle specular reflectance of light from these defects. Larger flaws, which are also detrimental to producing clear images in the electrophotographic imaging process, are referred to as high frequency surface flaws.

Low frequency specular surface flaws can be categorized by their thickness difference with respect to the mean coating thickness. For example, in a coating having a thickness of about 25 µm, flaws in the coating on the order of about 1 µm or less may be categorized as Level 0 (zero) flaws; flaws on the order of about 5 µm peak-to-peak (about 1.7 µm peak-to-reference, where reference is the nominal level of the exterior coating) categorized as Level 1 (one) flaws; flaws on the order of about 7.5 µm peak-to-peak (about 5 µm peak-to-reference) may be categorized as Level 2 flaws; and flaws on the order of about 21 µm peak-to-peak (about 18 µm peak-to-reference) may be categorized as Level 3 flaws. Larger flaws are considered high frequency surface flaws.

Low frequency specular surface flaws and high frequency surface flaws detrimentally affect the performance of the OPC drum photoreceptor in reproducing images. Flaws as small as about 1 µm can have a detrimental effect on the reproduced image. As indicated, the flaws are areas of different coating thicknesses, and as such they have different charging and discharging properties as compared with the flawless areas of the coating and as compared with each other. This typically results in banding on the final image. This is even more critical in high speed color xerographic engines where color registration is critical for true color image reproduction.

Machine vision inspection methods for detecting surface flaws, in general, include dark field angle, use of broad structured light, and laser profiling, for example as taught in U.S. Pat. No. 6,157,450, the disclosure of which is incorporated herein by reference in its entirety. These methods, however, have proved not to be useful in detecting low frequency specular surface flaws on coated substrates. Low frequency specular surface flaws of Level 3 or lower can only currently be observed by manual visual inspection. This method is tedious, inefficient, costly, and time consuming. A cost efficient, automated surface flaw detection apparatus is needed.

The disclosure contained herein describes attempts to address one or more of the problems described above.

SUMMARY

In an embodiment, a method for detecting a specular surface flaw on a coated substrate includes impinging visible non-integrated light from a linear electromagnetic radiation source onto a coated substrate. The visible non-integrated light may be reflected off the coated substrate into a first photosensitive device to form a high frequency surface flaw image. In embodiments, visible coherent light from a coherent electromagnetic radiation source may be impinged onto the coated substrate at an oblique angle. The non-integrated visible light and the visible coherent light on the coated substrate may be collocated but not combined on the substrate. Embodiments include reflecting the visible coherent light off the coated substrate onto a screen material to form a low frequency surface flaw image. The low frequency surface flaw image may be recorded off the screen material with a recorder to form a recorded low frequency surface flaw image. The recorder, in embodiments, may be a manual visual inspector, a second photosensitive device, or a mixture thereof. In embodiments, at least one of the first photosensitive device and the recorder may include a charge-coupled device area scan detector.

In certain embodiments, the coated substrate may include a cylindrical drum. In other embodiments the coated substrate may be rotated about a rotational axis. Impinging the visible non-integrated light may form a line of visible non-integrated light along the rotational axis in some embodiments, and impinging the visible coherent light may form a line of visible coherent light along the rotational axis in further embodiments.

In embodiments, the linear electromagnetic radiation source may include a halogen lamp positioned to transmit visible electromagnetic radiation into a fiber optic line. In further embodiments, the fiber optic line may include a plurality of optical fibers, and the plurality of optical fibers may further include a corresponding plurality of fiber optic tips, and each, fiber optic tip may distributes a point source of light with the point sources of light lacking integration. In still further embodiments, the plurality of fiber optic tips may be maintained at a standoff distance of about 60 mm.

In several embodiments, visible coherent light may be impinged from a coherent electromagnetic radiation source, and that source may be selected from the group consisting of a laser, a fan laser, and a laser further comprising an optic lens system. In certain embodiments the visible coherent light may have a wavelength of about 660 nm. In yet other embodiments, the impinging visible coherent light may impinge from a direction that is substantially perpendicular with respect to the rotational axis.

Digitally processing the recorded low frequency surface flaw image and the high frequency surface flaw reflected image to determine a dimensional characterization of a specular surface flaw are included in embodiments herein.

In still yet another embodiment, an apparatus may include a first source that is positioned to direct visible non-integrated light onto a coated substrate, and a first photosensitive device positioned to receive a reflection of the visible non-integrated light off the coated substrate. The reflection of the visible light may be a high frequency flaw image.

In embodiments, a second source may be positioned to direct visible coherent light onto the coated substrate, and a screen material may be positioned to receive a reflection of the visible coherent light off of the coated substrate. Embodiments include a second photosensitive device positioned to record a low frequency surface flaw image from the screen material.

In embodiments, the apparatus may further include a motor that rotates the coated substrate along a rotational axis of the substrate.

In several embodiments the first source may include a halogen lamp positioned to transmit visible electromagnetic radiation into a fiber optic line, and the fiber optic line may include a plurality of optical fibers. The plurality of optical fibers may further include a corresponding plurality of fiber optic tips.

The apparatus embodied herein, may have the second source selected from the group consisting of a laser, a fan laser, and a laser with an optic lens system.

In other embodiments, at least one of the first and second photosensitive devices may be a charge-coupled device area scan detector camera.

In addition, some embodiments include a digital processing system to determine a dimensional characterization of a surface flaw.

In still another embodiment, a method of detecting a specular surface flaw on an organic photoconductor drum may include rotating an organic photoconductor drum about a rotational axis of the drum, while impinging non-integrated light from a first source along the rotational axis of the drum. The first source may include a plurality of optical fibers, and each fiber further includes a fiber optic tip that distributes a point source of light.

Reflecting the non-integrated light off the drum into a first camera to form a recorded high frequency surface flaw image is an embodiment herein.

In some embodiments, coherent laser light from a laser may be impinged onto the drum at an oblique angle. In several embodiments, the coherent laser light may have a wavelength of about 660 nm. In several embodiments, the non-integrated light and the coherent laser light on the drum may be collocated but not combined on the drum. The coherent laser light may be reflected off the drum onto a screen material to form a low frequency surface flaw image, and the low frequency surface flaw image may be recorded off the screen material with a second camera to form a recorded low frequency surface flaw image.

In still other embodiments, the recorded low frequency surface flaw image and the recorded high frequency surface flaw image may be digitally processed to determine a dimensional characterization of a specular surface flaw.

DETAILED DESCRIPTION

Before the present methods, systems and materials are described, it is to be understood that this disclosure is not limited to the particular methodologies, systems and materials described, as these may vary. It is also to be understood that the terminology used in the description is for the purpose of describing the particular versions or embodiments only, and is not intended to limit the scope. For example, as used herein and in the appended claims, the singular forms "a," "an," and "the" include plural references unless the context clearly dictates otherwise. In addition, the word "comprising" as used herein is intended to mean "including but not limited to." Unless defined otherwise, all technical and scientific terms used herein have the same meanings as commonly understood by one of ordinary skill in the art. All of the patent publications mentioned herein are incorporated herein in their entireties. The optic terms "point sources", "linear electromagnetic radiation source" and "coherent light" are used herein in an informal, practical sense, as would be practiced by one of ordinary skill in the art Referring to FIGS. 1-3, an embodiment of an apparatus that includes a plural light source and camera to detect low frequency specular surface and high frequency flaws 50 is depicted. The apparatus may include a high frequency flaw detection unit 52. The high frequency flaw detection unit 52 may include a linear visible non-integrated electromagnetic radiation source 55 as a first source. The first source is positioned to direct visible non-integrated light onto a coated substrate. Light that lacks integration or non-integrated light refers to light from individual point sources of light, which may impinge on and reflect off a coated substrate at various angles, and which may enhance the contrast of high frequency surface flaws on a coated substrate such as, but not limited to, an OPC drum. A linear visible non-integrated electromagnetic radiation source 55 may include an incoherent light source. An incoherent light source may emit electromagnetic radiation of more than one wavelength. In an embodiment, the linear non-integrated electromagnetic radiation source 55 may include a halogen lamp positioned to transmit visible light into a fiber optic line 60. The fiber optic line 60 may include a plurality of optical fibers (not shown), and the plurality of optical fibers include a corresponding plurality of optical fiber tips 65 at the emitting end 70. In some embodiments, the plurality of fiber optic tips 65 may be arranged in a substantially linear configuration, which may include a single row or multiple rows of fiber optic tips 65. In the exemplary embodiment of FIG. 3, the plurality of fiber optic tips 65 are arranged in a definite rectangular "3×6" pattern. It is recognized that other patterns, such as square patterns and random patterns for the plurality of fiber optic tips 65 could be used. It is also recognized that the actual number of fiber optic tips 65 can be any number greater than one (1), with the upper limit depending upon the area to be scanned and the desired contrast of the recorded specular surface flaw image. Increasing the number of fiber optic tips 65 serves to increase contrast of the recorded specular surface flaw image.

In an embodiment, for example, the diameter of each optical fiber is about 100 µm. Any suitable fiber optic materials may be used for these embodiments: for example, including but not limited to Fostec Light Line part #A08912 D (SCHOTT North America, Inc.). Persons having ordinary skill in the art will recognize that other standard or non-standard fiber optic fibers, optic fiber bundles, and optic fiber materials can be used in the embodiments described herein.

Figure 3:
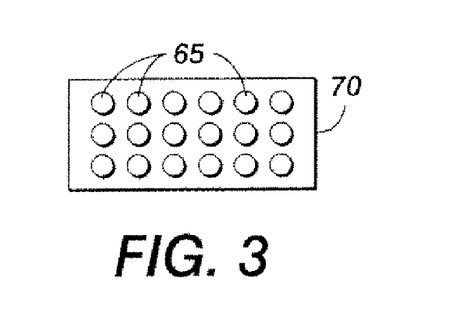
FIG. 3 depicts a plurality of fiber optic tips at an emitting end of an optic light line.
Figure 4:
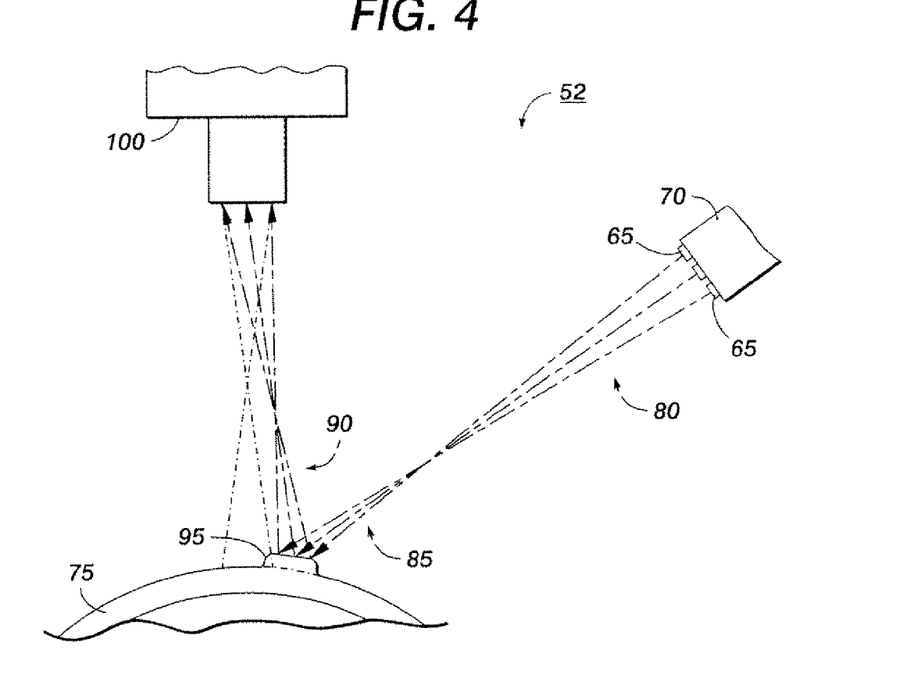
FIG. 4 depicts non-integrated light waves from a high frequency surface flaw detection unit to detect high frequency surface flaws.

In one embodiment, the emitting end 70 that includes the plurality of fiber optic tips 65 may be placed at about 5 mm to about 200 mm from the coated substrate 75. This distance is referred to herein as the standoff or standoff distance. In another embodiment, the standoff is about 10 mm to about 100 mm. In yet another embodiment, the standoff is about 60 mm. The intensity of the point source of light that is emitted from each of the fiber optic tips 65 diminishes with increasing standoff distance.

Referring now to FIGS. 1-4, each individual fiber optic tip in the plurality of fiber optic tips 65 functions as an individual light source to distribute a point source of light when the linear electromagnetic radiation source 55 is activated. The plurality of fiber optic tips 65 are placed in proximity of a coated substrate 75 such that they emit visible non-integrated electromagnetic radiation 80 incident at various angles onto the coated substrate 75. As such, each point source of light emitted from the plurality of fiber optic tips 65 is incident on the coated substrate 75 at different angles 85. No focusing lens is used in between the plurality of fiber optic tips and the OPC drum. As such, the emitted light lacks integration or is non-integrated. A lack of integration of light emitted from the plurality of optic tips 65 results in the light from individual fiber optic tips to be incident on the OPC drum at various angles. This results in reflection, of the light to occur at various angles 90. Since the light is reflected from the surface at various angles 90, the contrast of the coating on the OPC drum is enhanced, enabling high frequency flaw detection of a coated OPC drum specular surface. When the substrate 75 includes a high frequency surface flaw 95 the reflected light forms a high frequency surface flaw reflected image.

Figure 1:
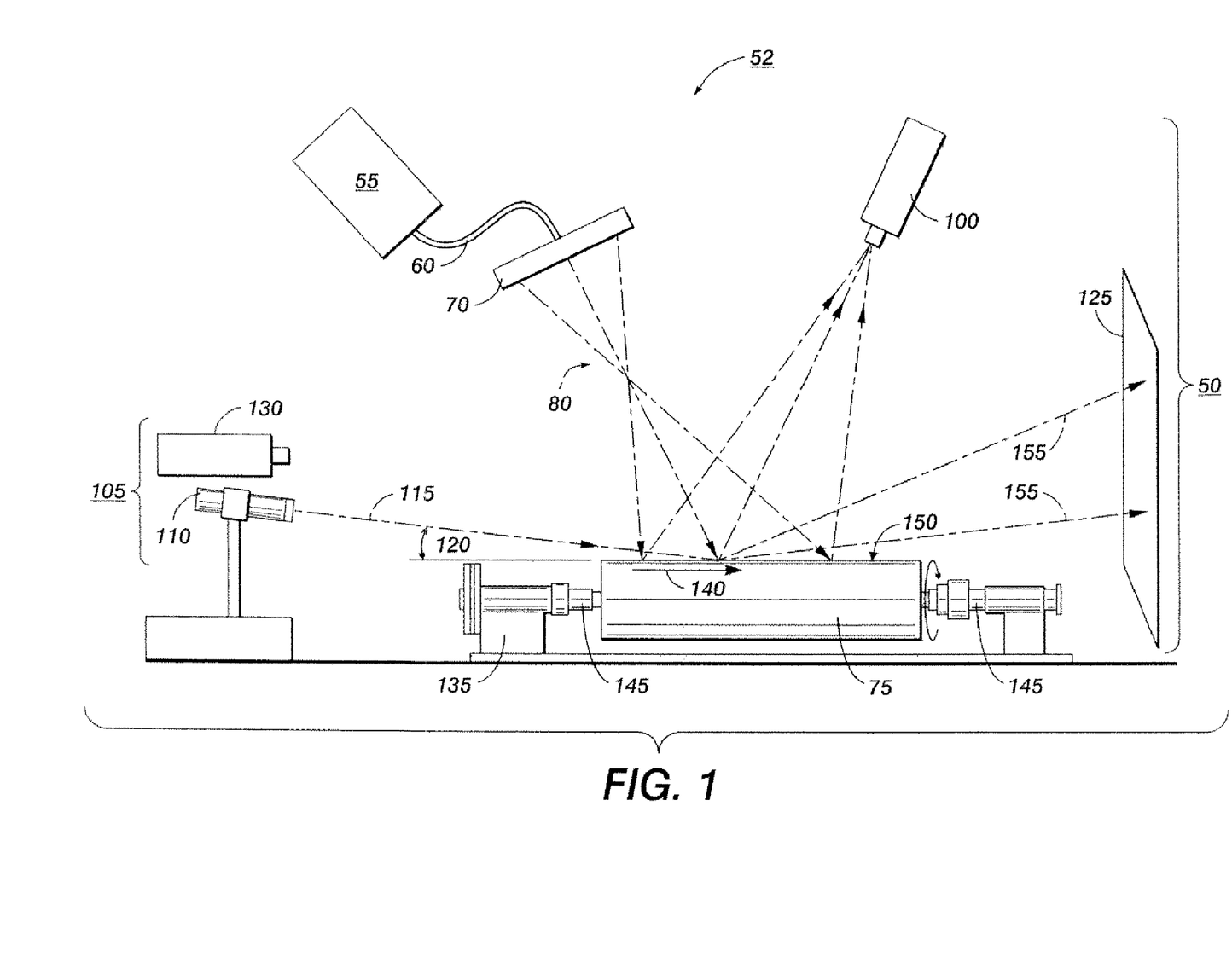
FIG. 1 illustrates an exemplary embodiment of an apparatus that includes a plural light source and camera to detect low and high frequency surface flaws.
Figure 2:
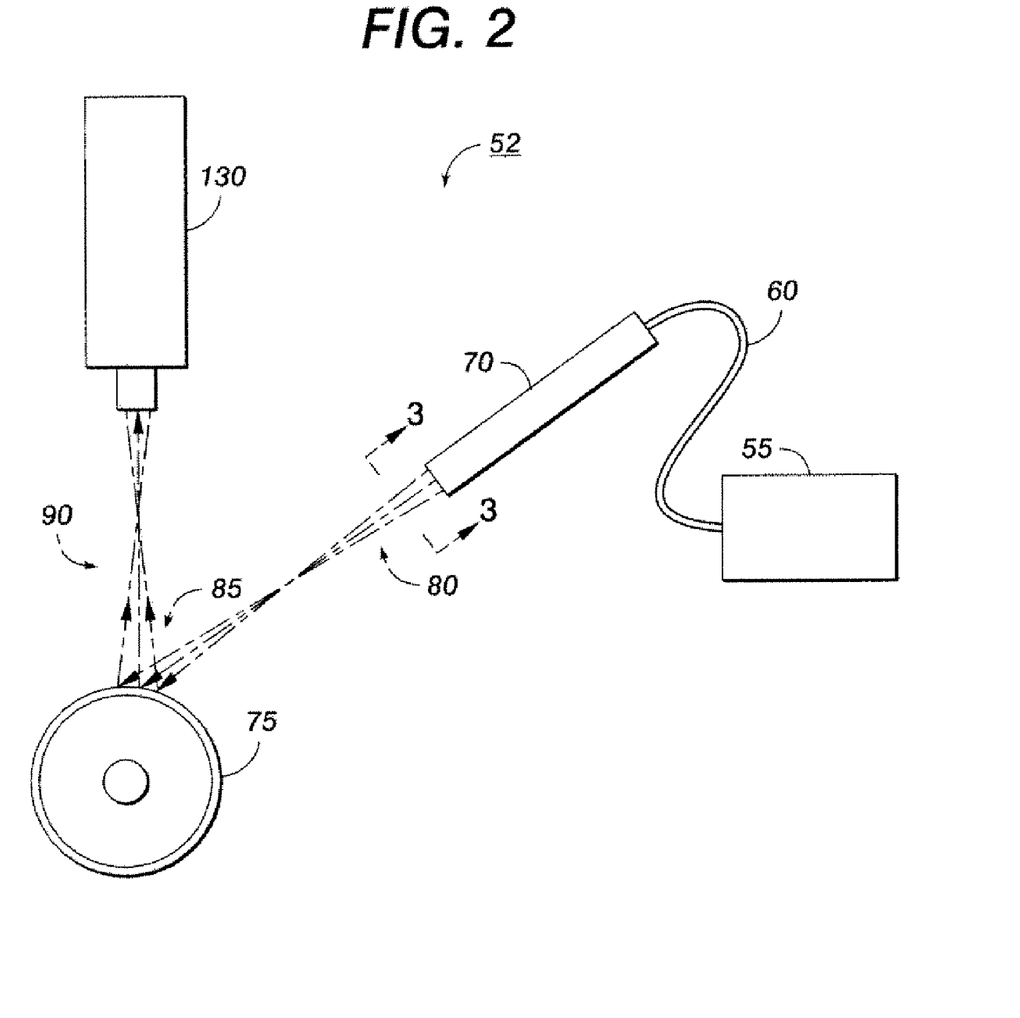
FIG. 2 depicts a high frequency surface flaw detection unit of a plural light source and camera apparatus to detect low frequency specular surface flaws and high frequency surface flaws.

The apparatus may further include a first photosensitive device 100 positioned above the coated substrate 75 in order to directly receive and record the high frequency surface flaw image. In an embodiment, the first photosensitive device 100 may include a camera. The camera may be of the film-type, which typically use emulsion photographic films to capture images, or of the digital type. An embodiment of a camera may include a charge-coupled device (CCD) area scan camera. In yet another embodiment, the camera may include a line scan camera. Another embodiment for a first photosensitive device 100 may include an area scan complementary metal-oxide-semiconductor (CMOS) device.

In a further embodiment, the recorded reflected high frequency surface flaw image may be subjected to digital image processing to determine flaw dimensional characteristics. The image captured by the first photosensitive device 100 may be digitally processed using a computer (not shown) and digital imaging processing software, which are known to persons having ordinary skill in the art and can be adapted for the purposes of embodiments herein.

Figure 5:
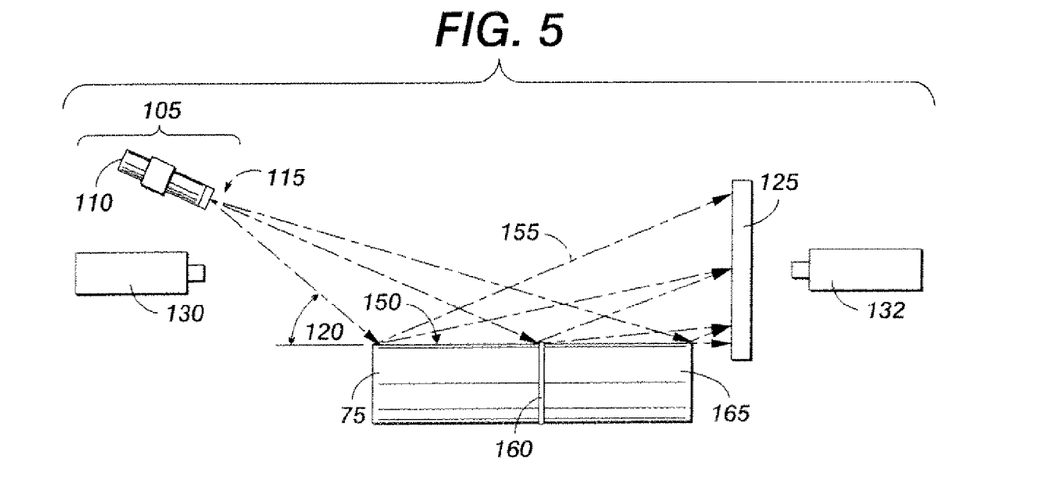
FIG. 5 depicts a low frequency surface flaw detection unit of a plural light source and camera apparatus to detect low frequency specular surface and high frequency flaws.

Referring now to FIGS. 1 and 5, the apparatus 50 further includes a low frequency flaw detection unit 105. The low frequency flaw detection unit 105 includes a substantially coherent electromagnetic radiation source 110 as a second source. The substantially coherent electromagnetic radiation source may be referred to herein interchangeably as a coherent electromagnetic radiation source or simply as a second source. The second source is positioned to direct visible coherent light onto the coated substrate. Coherent electromagnetic radiation or coherent light is light in which the electromagnetic waves maintain a fixed and predictable phase relationship with each other over a period of time. In an embodiment, a coherent electromagnetic radiation source 110 may include a laser, and the laser may emit monochromatic light. In another embodiment the monochromatic light may have a frequency of about 660 nm.

The coherent electromagnetic radiation source 110 may include a fan laser, which illuminates a line or stripe of visible electromagnetic radiation, or a laser comprising an optic lens system (not shown) to provide an even distribution of visible coherent light on the coated substrate 75. The even distribution of visible coherent light may be in the form of a line across the substrate 75. The coherent electromagnetic radiation source 110 emits visible coherent light 115 at an oblique angle 120 with respect to the coated substrate 75 surface. One embodiment may use an oblique angle 120 of the visible coherent light with respect to the coated substrate 75 surface of about 1° to about 80°. Another embodiment may use an oblique angle 120 for the visible coherent light of about 3° to about 45°. Yet another embodiment may use an oblique angle 120 of about 9°.

The apparatus 50 of an embodiment further includes a screen material 125. The screen material 125 may be any flat or nearly flat, white or nearly white material that yields a sharp image of the low frequency specular surface flaw reflected image, such as cloth or other textiles, matte white fiberglass, vinyl or other material. Alternatively, the screen material 125 may be transparent, nearly transparent, or translucent, resulting in a low frequency specular surface flaw transmitted image.

In an embodiment of an apparatus 50, a second photosensitive device 130 or 132 is positioned to record the low frequency surface flaw image off of the screen material 125. In an embodiment where the screen material 125 is reflective, the second photosensitive device 130 may be positioned in front of the screen material 125 or on the same side of the screen material 125 as the coherent electromagnetic radiation source 110. Alternatively, in embodiments where the screen material 125 is transparent, nearly transparent, or translucent, the second photosensitive device 132 may be positioned behind the screen material 125, or on the side opposite of the coherent electromagnetic radiation source 110. A second photosensitive device 130 or 132 may include a suitably sensitive camera, and the camera may be of the film-type, which typically use emulsion photographic films to capture images, or of the digital type. A camera in one embodiment may include a charge-coupled device (CCD) area scan camera. Another embodiment may include a line scan camera. Yet another embodiment of a camera for the second photosensitive device may include an area scan complementary metal-oxide-semiconductor (CMOS) device.

In one specific, but not limiting example, when a coated substrate 75 was a 357 mm long OPC drum, a laser 110 was positioned 7¾ inches from an end of the drum to direct the laser beam toward the drum at an approximately 20° angle. The screen 125 was positioned 18 inches from the other end of the drum.

Optionally the apparatus 50 further includes a coated substrate rotating mechanism 135. A coated substrate may have a rotational axis 140, such as a longitudinal axis. The rotating mechanism 135 may include an electric motor integrally attached to a coated substrate suspending member 145. It is recognized that rotating mechanisms other than an electric motor, for example but not limited to a battery operated motor, are effective for the apparatus 50 to detect high and low frequency specular surface flaws.

In an embodiment that includes the use of the apparatus to detect high and low frequency specular surface flaws on a coated substrate which is an OPC drum, a rotation speed of the drum may be about 1 revolution per minute (rpm) to about 100 rpm. In another embodiment, a rotation speed may be about 40 rpm to about 60 rpm. In another embodiment, a rotation speed of the drum may be about 50 rpm. It should be recognized that faster rotation speeds of the coated substrate may expedite the flaw detection, and that the rotation speed is currently only limited by the camera frame rate and the number of pixels available for digital image processing. However, it should also be recognized that rotation is not required to practice the embodiments described herein, and the methods described may be used on coated cylindrical objects, coated flat objects, or other surfaces.

In the embodiment of FIGS. 1 and 5, the coherent electromagnetic radiation source 110 impinges a line of visible coherent light along the coated substrate 75 from a direction that is substantially parallel with the longitudinal or rotational axis 140. In other embodiments, (see FIGS. 6-7) the coherent electromagnetic radiation source 110 may impinge a line of visible coherent electromagnetic radiation along the coated substrate 75 from a direction that is substantially perpendicular with the longitudinal or rotational axis 140. The impinging visible coherent light may impinge from a direction that is substantially perpendicular with respect to the rotational axis. It is recognized that all directions of impingement of the coherent electromagnetic radiation source 110 onto the coated substrate 75 are within the scope of embodiments herein, as long as the visible coherent electromagnetic radiation impinges the coated substrate 75 at an oblique angle 120, and it is able to be recorded by the second photosensitive device 130 or by a suitable recorder.

Now referring to FIG. 5 an embodiment for detecting low frequency specular surface flaws on a coated substrate 75, which includes an OPC coated drum, is depicted. The coated substrate 75 is optionally rotated with a rotating mechanism 135 (see FIG. 1). A line of visible coherent light 150 is emitted from a visible coherent electromagnetic radiation source 110. The visible coherent electromagnetic radiation source is interchangeably referred to herein as the coherent electromagnetic radiation source or simply the second source. In the embodiment shown, this may be achieved using a laser, a fan laser, or a laser comprising an optic lens system to provide a line of coherent visible light 150 on the coated substrate 75. Visible electromagnetic radiation 150 with a wavelength of approximately 660 nm is used in various embodiments, but it is recognized that any wavelength of visible light will work for embodiments herein. In some embodiments, a narrow bandwidth laser of about 29 nm (+/−3%) may be used. The line of visible coherent light 150 reflects off of the coated substrate 75 as reflected electromagnetic radiation 155 to form a low frequency specular surface flaw reflected image on the screen material 125. Low frequency specular surface flaws 160 are represented in the specular surface flaw reflected image in differences in contrast from the flawless coating area 165. The specular surface flaw reflected image on the screen material 125 is recorded using a recorder, which may include a second photosensitive device 130 and the image may be digitally processed using a computer (not shown) and digital imaging processing software, which are known to persons having ordinary skill in the art.

Figure 6:
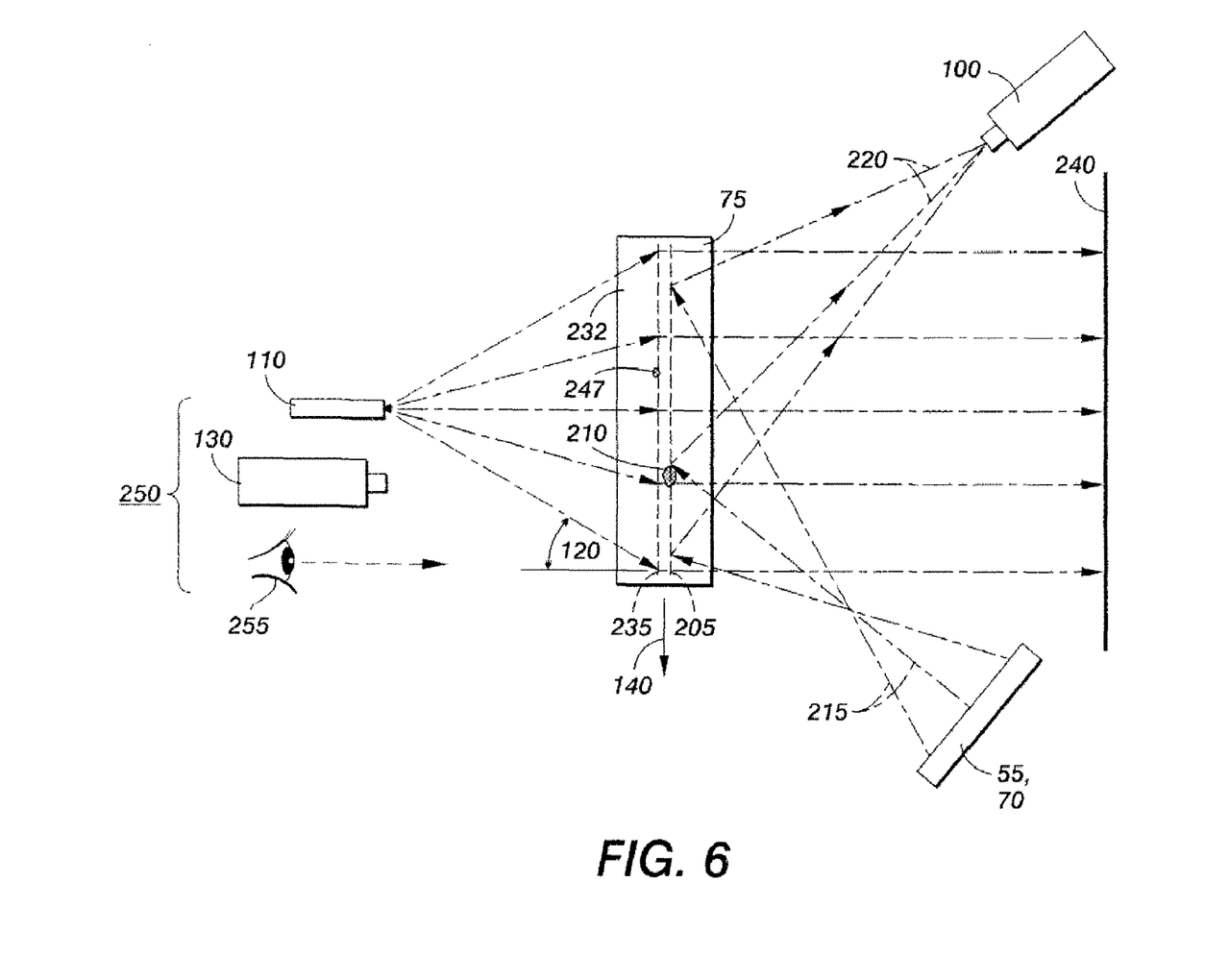
FIG. 6 depicts an embodiment of a method and apparatus of a plural light source and camera apparatus to detect low frequency specular surface and high frequency flaws using a reflective screen material.
Figure 7:
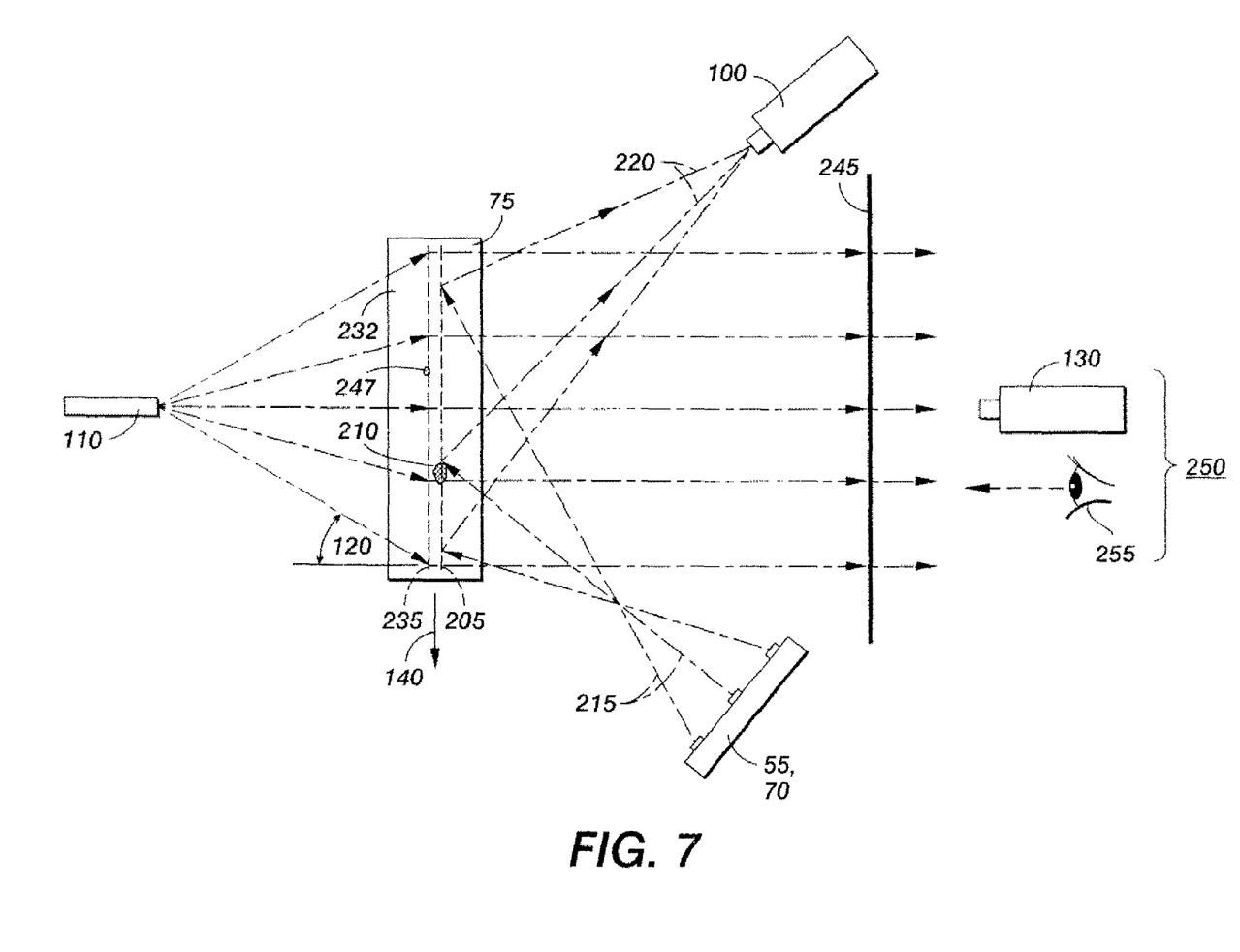
FIG. 7 depicts an embodiment of a method and apparatus of a plural light source and camera apparatus to detect low frequency specular surface and high frequency flaws using a translucent screen material.

FIG. 6 depicts an arrangement for detecting high and low frequency flows on a coated substrate including an embodiment utilizing a reflective screen material. FIG. 7 depicts an arrangement for detecting high and low frequency flows on a coated substrate including an embodiment utilizing a translucent screen material.

In each of FIGS. 6 and 7, the coated substrate 75 may be optionally rotated with a rotating mechanism (not shown). The arrangements of the plural light source and camera in FIGS. 6 and 7 enable the simultaneous detection of high and low frequency surface flaws. For determining high frequency surface flaws, in each of the embodiment of FIGS. 6 and 7, a line of visible non-integrated light 205 may be impinged on the coated substrate 75 from a linear non-integrated electromagnetic radiation source 55. The line of visible non-integrated light 205 is reflected off of the coated substrate 75 directly into a first photosensitive device 100. The first photosensitive device 100 may include a suitably sensitive film or digital camera, a CCD area scan camera, or a CMOS device. When the coated substrate includes a high frequency flaw 210, the contrast of the reflected flaw image is enhanced due to the lack of integration of the impinging 215 and reflected light 220. The image of the high frequency flaw is recorded by the first photosensitive device 100 to form a recorded high frequency surface flaw image.

Figure 8:
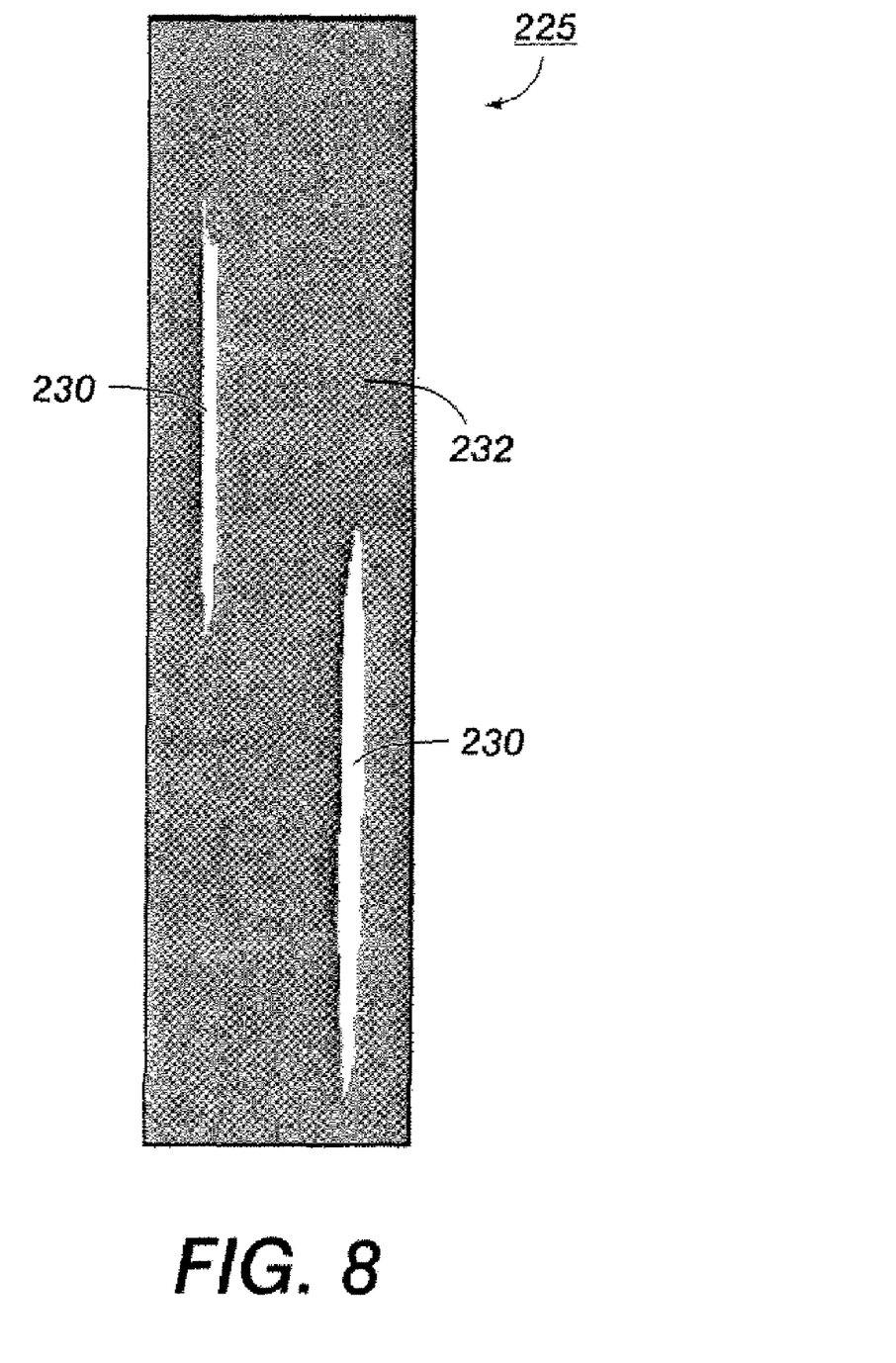
FIG. 8 is a reproduction of a recorded high frequency surface flaw image obtained by an embodiment of a plural light source and camera apparatus.

A black and white reproduction of a high frequency surface flaw reflected image 225 from a coated substrate OPC drum is presented in FIG. 8. The high frequency surface flaws appear in the reflected image 225 as light areas 230, as compared with the areas in the image of the flawless areas 232. The flaw images 230 appear light in the reflected image 225 due to differences in interference of the reflected electromagnetic radiation from flawed and flawless areas on the coated substrate OPC drum. This is a result of the lack of integration of the light that is emitted form each point source of each fiber optic tip. In various experiments, flaws having a peak to peak size as small as 21 μm were detected using high frequency surface flaw detection embodiments herein.

Using a suitably sensitive first photosensitive device to record the high frequency surface flaw reflected image off of a coated substrate may provide detection of flaws down to the size of Level 3, or about 21 μm peak-to-reference, or less. This flaw detection level was obtained, for example, when the first photosensitive device included an area scan charge-coupled device (CCD) camera.

The plural light source and camera of embodiments herein simultaneously detects high frequency and low frequency specular surface flaws, and both detection schemes are depicted on FIGS. 6 and 7. The high frequency flaws are detected as disclosed above. To detect low frequency flaws, a substantially coherent light source is used, such as a laser, and the reflected image that results from a low frequency flaw is projected onto a screen. It is recognized that the visible non-integrated light for detecting high frequency flaws, and the visible coherent light for detecting low frequency flaws do not have to impinge on the coated substrate in the form of a line. Any geometrical shape of the footprint of the impinging two forms of light on the substrate, such as a circle or other geometrical shape, are within the scope of embodiments herein, as long as the footprint provides the resolution to detect the various surface flaws. When the apparatus and the method are used in embodiments for OPC drums, rotating the drum and using a line of visible non-integrated light and a collocated line of visible coherent light, it is possible to rapidly detect high and low frequency defects over the entire coated surface of an OPC drum.

Referring again to embodiments in FIGS. 6-7, a line of visible coherent light 235 from a coherent electromagnetic radiation source 110 may be impinged on the coated substrate 75 at an oblique angle 120. In an embodiment, the coherent electromagnetic radiation source 110 may include a laser, a fan laser, or a laser equipped with an optic lens system to provide a line of coherent visible light 235 on the coated substrate 75. The line of visible coherent light 235 may be collocated to the line of visible non-integrated light 205, but not combined on the substrate 75. "Collocated" as used herein indicates that the visible coherent light is near the visible non-integrated light on the coated substrate, but the two forms of light do not overlap or combine on the coated substrate. The two forms of light may impinge on the coated substrate at the same time, but do not overlap.

The line of visible coherent electromagnetic radiation 235 is reflected off the coated substrate 75 to a screen material 240 or 245 forming a low frequency flaw image when a low frequency flaw 247 is present on the coated substrate 75. In an embodiment, the screen material may be a reflective screen material 240 (see FIG. 6). In another embodiment, the screen material may be a translucent screen material 245 (see FIG. 7). A recorder 250 may record the low frequency flaw image. The term "recorder", as used herein includes a person looking at the image and conducting a manual visual inspection 255, and/or a second photosensitive device 130 capturing the image so that it may be viewed at a later time or digitally processed to determine flaw dimensions. In an embodiment, a person may be looking at the image on the screen material 240 or 245 and conducting a visual inspection 255 of the image on the screen material 240 or 245. For example, a visual inspection may be able to result in a quick acceptance or rejection of coated OPC drums in a quality control situation based on detection of a certain size or number of low frequency flaws. Proper safety procedures to protect the inspector from directly viewing the laser radiation should be followed. In an embodiment at least one of the first photosensitive device and the recorder comprises a charge-coupled device area scan detector.

The recorder 250 is positioned to record the low frequency specular flaw image from the screen material 240 or 245. Referring to FIG. 6, using a reflective screen material 240, the recorder 250 may be positioned on the front side of the screen material 240, that is the same side as the coherent electromagnetic radiation source 110. Referring to FIG. 7, using a translucent screen material 245, the recorder 250 may be positioned on the backside of the screen material 245, that is the side opposite of the coherent electromagnetic radiation source 110. In embodiments using a translucent screen material 245, such as that shown in FIG. 7, there may be afforded more flexibility in positioning the recorder 250.

Figure 9:
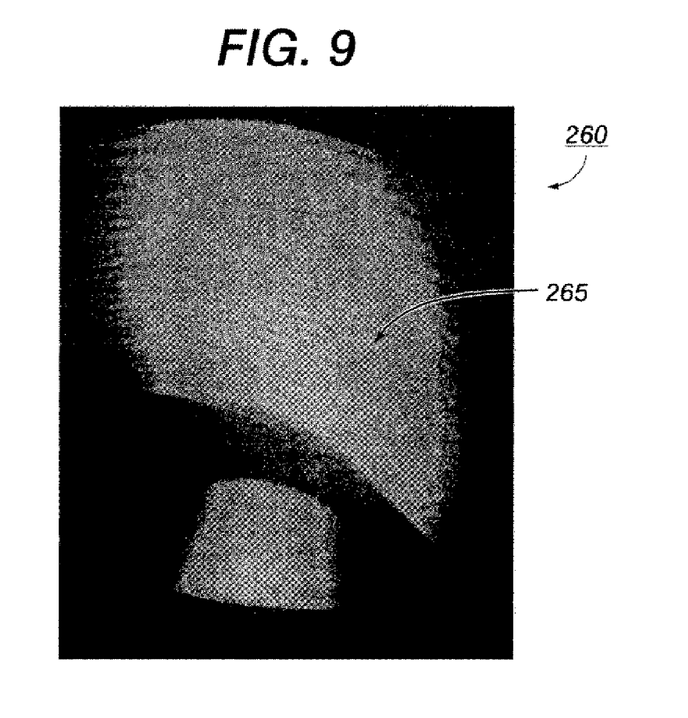
FIG. 9 is a reproduction, of a recorded low frequency surface flaw image obtained by an embodiment of a plural light source and camera apparatus.

Now referring to FIG. 9, a black and white reproduction is presented of a low frequency specular surface flaw image 260 from a coated substrate where the substrate is an OPC drum, and contains a low frequency surface flaw. The low frequency surface flaws in the image 260 appear as areas of varying contrast 265, and for this case have a periodic band nature. The flaws appear as areas of varying contrast 265 in the image 260 due to differences in interference of the reflected electromagnetic radiation from flawed and flawless areas.

The use of the screen material to form the low frequency specular surface flaw image is important for the disclosed embodiments. Using a second photosensitive device to record the low frequency specular surface flaw image off a screen material may provide detection of flaws down to the size of Level 0, or 1 µm or less. Attempting to directly record the low frequency specular surface flaw image with a photosensitive device (i.e., reflecting the light directly into the camera with no screen material) does not result in the detection of flaws on the small size levels described herein. Thus, the present embodiments assist in the detection of smaller coating surface flaws than were previously possible.

In various embodiments, coating thickness measurements using, for example, a Permascope and form gauge revealed that the height of these low frequency specular surface flaws or defects depicted in the specular surface flaw reflected image of FIG. 9 was on the order of 0.75 µm, that is, Level 0 defects.

It is recognized that the low frequency surface flaw detection unit 105 (see FIGS. 1 and 5) can be used to detect larger high frequency flaws but does not provide the image quality and resolution of the high frequency flaws, as does the high frequency flaw detection unit 52 (see FIGS. 1-4).

Figure 10:
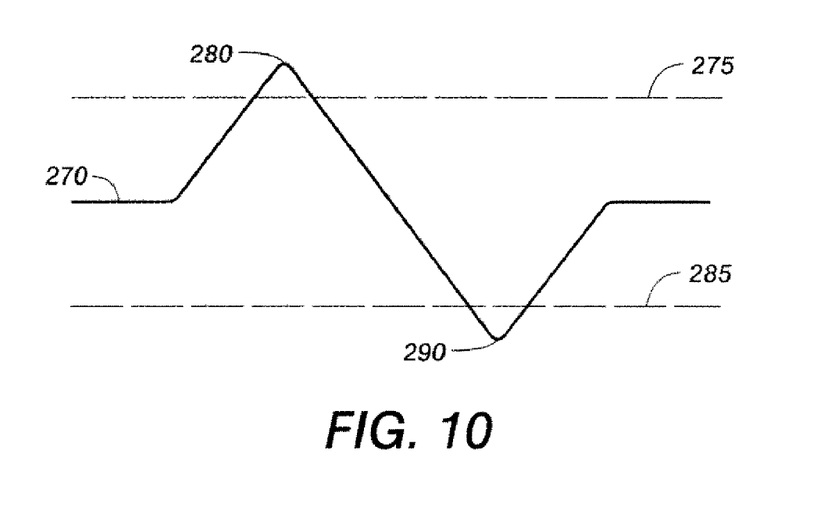
FIG. 10 depicts a method of digitally characterizing dimensional characteristics of a surface flaw.

Optionally, any suitable image processing technique may be used to detect variations in the captured flaw image, and to calculate dimensional characteristics of both high and low frequency specular surface flaws. For example, referring to FIG. 10, a portion of the reflected image in the high frequency detection unit and/or the low frequency detection unit may be processed on a pixel-by-pixel basis, and flaws may be indicated by measuring an intensity level 270 for each pixel. If a pixel intensity level exceeds an upper threshold 275 it may indicate a defect 280. Similarly, if a pixel intensity level is lower than a lower threshold 285, it may indicate a different type of defect 290.

In still another embodiment, a method of detecting a specular surface flaw on an organic photoconductor (OPC) drum may include rotating the drum about a rotational axis of the drum, while impinging non-integrated light on the drum from a first source along the rotational axis of the drum. The first source may include a plurality of optical fibers, and each fiber may include a fiber optic tip that distributes a point source of light. In an embodiment, the method may include reflecting the non-integrated light off the drum into a first camera to form a recorded high frequency surface flaw image. A method may include impinging coherent laser light onto the drum at an oblique angle, wherein the non-integrated light and the coherent laser light on the drum are collocated but not combined on the drum. The non-integrated light and the coherent laser light may impinge the drum in the form of lines that are coaxial with the rotational axis of the drum. In a method, the coherent laser light may be reflected off the drum onto a screen material to form a low frequency surface flaw image. The surface flaw image may be recorded off the screen material with a second camera to form a recorded low frequency image.

In an embodiment, the coherent laser light may have a wavelength of about 660 nm. It is recognized that laser light of any visible wavelength are within the scope of embodiments herein.

In still another embodiment, the recorded low frequency surface flaw image and the recorded high frequency surface flaw image obtained from the OPC drum may be digitally processes to determine a dimensional characterization of a surface flaw.

A first and/or a second camera may include a film camera, a digital camera, an area scan charge coupled device, a CMOS device, a line scan camera, or any other photosensitive device capable of providing suitable resolution and quality of the images. A suitable camera may also include a movie camera, camcorder, or webcam. The screen material may be of any stable composition and may be reflective or translucent.

In a further embodiment, the recorded low frequency surface flaw image and the recorded high frequency surface flaw image may be digitally processed to determine the number and the dimensional characteristics of specular surface flaws on an OPC drum.

Figure 11:
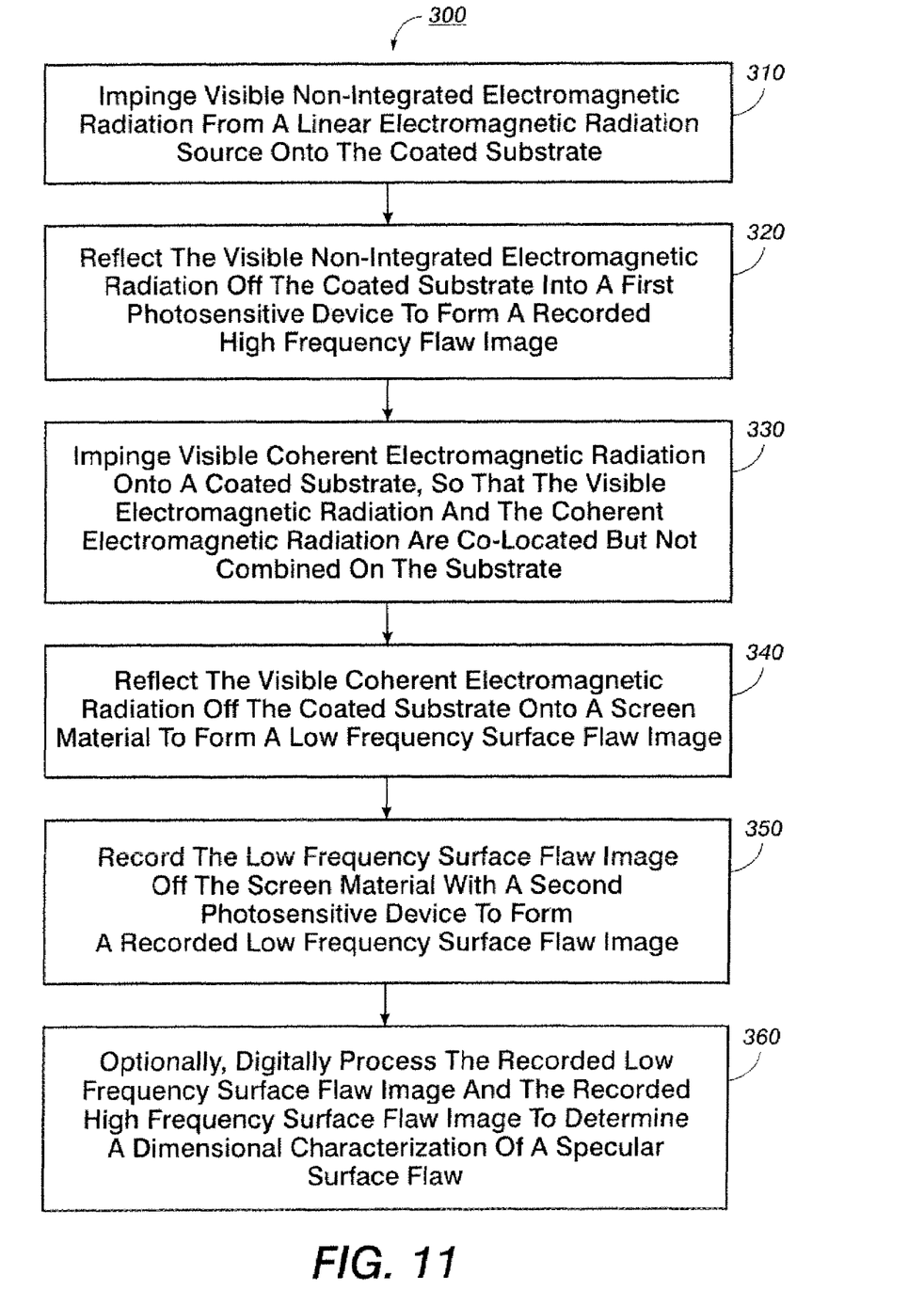
FIG. 11 is a flow diagram of a method using a plural light source and camera apparatus to detect low frequency specular surface and high frequency flaws.

An exemplary method of using a plural lighting source and camera apparatus to detect high and low frequency surface flaws 300 is presented in FIG. 11. In an embodiment, visible non-integrated electromagnetic radiation from a linear electromagnetic radiation source may be impinged onto a coated substrate 310. The visible electromagnetic radiation may be reflected off the coated substrate into a first photosensitive device to form a recorded high frequency flaw image 320. Visible coherent electromagnetic radiation is impinged onto the coated substrate, so that the visible non-integrated electromagnetic radiation and the coherent visible radiation are collocated, but not combined on the coated substrate 330. The visible coherent electromagnetic radiation may be reflected off of the coated substrate onto a screen material to form a low frequency specular surface flaw image 340. A second photosensitive device may be used to record the low frequency specular surface flaw image 350. Optionally, the recorded low frequency flaw image and the recorded high frequency flaw image may be digitally processed to determine dimensional characteristics of a specular surface flaw 360.

It will also be recognized that the embodiments described herein may be used on various substrates with transparent coatings. For example, an OPC drum may be coated with any suitable coating or coatings to fabricate a photosensitive imaging member. Such coatings may include multi-layer coatings, such as a barrier uncoat material (UCM), and may be applied, along with a charge generating material (CGM) and a charge transport material (CTM). The CGM and CTM may be in different layers or in a single layer along with a binder resin. Typical organic photoconductive CGMs include, for example, one or more of azo pigments, such as Sudan Red, Dian Blue, Janus Green B, and the like; quinone pigments such as Algol Yellow, Pyrene Quinone, Indanthrene Brilliant Violet RRP, and the like; quinocyanine pigments; perylene pigments; indigo pigments such as indigo, thioindigo, and the like; bisbenzoimidazole pigments such as Indofast Orange toner, and the like; phthalocyanine pigments such as copper phthalocyanine, aluminochloro-phthalocyanine, titanyl phthalocyanine, hydroxy gallium phthalocyanine and the like; quinacridone pigments; or azulene compounds. Typical inorganic photoconductive CGMs include, for example, cadmium sulfide, cadmium sulfoselenide, cadmium selenide, crystalline and selenium, lead oxide and other chalcogenides.

Typical CTMs include, for example, one or more organic polymer or non-polymeric materials capable of supporting the injection of photoexcited holes or transporting electrons from the photoconductive material and allowing the transport of these holes or electrons through the organic layer to selectively dissipate a surface charge. Typical CTMs may also include, for example, a positive hole transporting material selected from compounds having in the main chain or the side chain a polycyclic aromatic ring such as anthracene, pyrene, phenanthrene, coronene, and the like, or a nitrogen-containing hetero ring such as indole, carbazole, oxazole, isoxazole, thiazole, imidazole, pyrazole, oxadiazole, pyrazoline, thiadiazole, triazole, hydrazone compounds, and the like. Other typical CTMs may include electron donor materials, such as carbazole; N-ethyl carbazole; N-isopropyl carbazole; N-phenyl carbazole; tetraphenylpyrene; 1-methyl pyrene; perylene; chrysene; anthracene; tetraphene; 2-phenyl naphthalene; azopyrene; 1-ethyl pyrene; acetyl pyrene; 2,3-benzochrysene; 2,4-benzopyrene; 1,4-bromopyrene; poly(N-vinylcarbazole); poly(vinylpyrene); poly(vinyltetraphene); poly(vinyltetracene), poly(vinylperylene), and the like. Typical electron transport materials include, for example, electron acceptors such as 2,4,7-trinitro-9-fluorenone; 2,4,5,7-tetranitro-fluorenone; dinitroanthracene; dinitroacridene; tetracyanopyrene, dinitroanthraquinone, and the like. The CTM may also incorporate an antioxidant such as butylated hydroxyl toluene to inhibit oxidation and deterioration of the CTM. The CTM may also incorporate poly(tetrafluoroethylene) (PTFE) in order to reduce wear and enable more efficient toner transfer.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for detecting a specular surface flaw on a coated substrate, comprising:
    impinging visible non-integrated light from a linear electromagnetic radiation source onto a coated substrate;
    reflecting the visible non-integrated light off the coated substrate into a first photosensitive device to form a high frequency surface flaw image;
    impinging visible coherent light from a coherent electromagnetic radiation source onto the coated substrate at an oblique angle, wherein the non-integrated visible light and the visible coherent light on the coated substrate are collocated but not combined on the substrate;
    reflecting the visible coherent light off the coated substrate onto a screen material to form a low frequency surface flaw image, and;
    recording the low frequency surface flaw image off the screen material with a recorder to form a recorded low frequency surface flaw image.

2. The method of claim 1, wherein the coated substrate comprises a cylindrical drum.

3. The method of claim 1, further comprising:
    rotating the coated substrate about a rotational axis;
    wherein the impinging of the visible non-integrated light forms a line of visible non-integrated light along the rotational axis; and
    wherein the impinging of the visible coherent light forms of a line of visible coherent light along the rotational axis.

4. The method of claim 1, wherein:
    the linear electromagnetic radiation source comprises a halogen lamp positioned to transmit visible electromagnetic radiation into a fiber optic line;
    the fiber optic line comprises a plurality of optical fibers;
    the plurality of optical fibers further comprises a corresponding plurality of fiber optic tips;
    each fiber optic tip distributes a point source of light; and
    the point sources of light lack integration.

5. The method of claim 4, further comprising maintaining the plurality of fiber optic tips at a standoff distance of about 60 mm.

6. The method of claim 1, further comprising impinging the visible coherent light from a coherent electromagnetic radiation source that is selected from the group consisting of a laser, a fan laser, and a laser further comprising an optic lens system.

7. The method of claim 1, wherein the visible coherent light comprises a wavelength of about 660 nm.

8. The method of claim 3, wherein the impinging visible coherent light impinges from a direction that is substantially perpendicular with respect to the rotational axis.

9. The method of claim 1, wherein the recorder is selected from the group consisting of a manual visual inspector, a second photosensitive device, and a mixture thereof.

10. The method of claim 1, wherein at least one of the first photosensitive device and the recorder comprises a charge-coupled device area scan detector.

11. The method of claim 1, further comprising digitally processing the recorded low frequency surface flaw image and the high frequency surface flaw reflected image to determine a dimensional characterization of a specular surface flaw.

12. An apparatus, comprising:
    a first source that is positioned to direct visible non-integrated light onto a coated substrate;
    a first photosensitive device positioned to receive a reflection of the visible non-integrated light off the coated substrate, wherein the reflection of the visible light comprises a high frequency flaw image;
    a second source that is positioned to direct visible coherent light onto the coated substrate;
    a screen material positioned to receive a reflection of the visible coherent light off of the coated substrate; and
    a second photosensitive device positioned to record a low frequency surface flaw image from the screen material.

13. The apparatus of claim 12 further comprising a motor that rotates the coated substrate along a rotational axis of the substrate.

14. The apparatus of claim 12, wherein:
    the first source comprises a halogen, lamp positioned to transmit visible electromagnetic radiation into a fiber optic line;
    the fiber optic line comprises a plurality of optical fibers; and
    the plurality of optical fibers further comprises a corresponding plurality of fiber optic tips.

15. The apparatus of claim 12, wherein the second source is selected from the group consisting of a laser, a fan laser, and a laser with an optic lens system.

16. The apparatus of claim 12, wherein at least one of the first and second photosensitive devices comprises a charge-coupled device area scan detector camera.

17. The apparatus of claim 12, further comprising a digital processing system to determine a dimensional characterization of a surface flaw.

18. A method of detecting a specular surface flaw on an organic photoconductor drum comprising:
    rotating an organic photoconductor drum about a rotational axis of the drum;
    impinging non-integrated light from a first source along the rotational axis of the drum, wherein the first source comprises a plurality of optical fibers, and each fiber comprises a fiber optic tip that distributes a point source of light;
    reflecting the non-integrated light off the drum into a first camera to form a recorded high frequency surface flaw image;

impinging coherent laser light from a laser onto the drum at an oblique angle, wherein the non-integrated light and the coherent laser light on the drum are collocated but not combined on the drum;

reflecting the coherent laser light off the drum onto a screen material to form a low frequency surface flaw image; and recording the low frequency surface flaw image off the screen material with a second camera to form a recorded low frequency surface flaw image.

19. The method of claim 18, wherein the coherent laser light comprises a wavelength of about 660 nm.

20. The method of claim 18, further comprising digitally processing the recorded low frequency surface flaw image and the recorded high frequency surface flaw image to determine a dimensional characterization of a specular surface flaw.

* * * * *